(12) United States Patent
Delhomme et al.

(10) Patent No.: US 7,129,704 B2
(45) Date of Patent: Oct. 31, 2006

(54) SYSTEM FOR MONITORING SALINITY IN A WATER WELL

(75) Inventors: Jean-Pierre Delhomme, Boulogne Billancourt (FR); Christian Jennevin, Moscow (RU); Philippe Souhaite, Paris (FR); Eric Veignat, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/500,256

(22) PCT Filed: Dec. 20, 2002

(86) PCT No.: PCT/EP02/14829

§ 371 (c)(1),
(2), (4) Date: Dec. 14, 2004

(87) PCT Pub. No.: WO03/056326

PCT Pub. Date: Jul. 10, 2003

(65) Prior Publication Data

US 2005/0077901 A1    Apr. 14, 2005

(30) Foreign Application Priority Data

Jan. 2, 2002    (FR) .................................. 02 00008

(51) Int. Cl.
*G01V 3/20*    (2006.01)
*E21B 47/10*    (2006.01)
(52) U.S. Cl. ..................................... 324/325; 73/152.18
(58) Field of Classification Search ..............................
73/152.18–152.22, 152.46, 152.54, 152.57;
340/853.1, 854.9, 855.2, 856.3; 324/323–325
See application file for complete search history.

(56) References Cited

U.S. PATENT DOCUMENTS

| 2,733,201 A | 1/1956 | Thompson |
| 4,854,728 A | 8/1989 | Baron et al. |
| 5,581,189 A | 12/1996 | Brenn |
| 6,158,276 A | 12/2000 | Patey et al. |

FOREIGN PATENT DOCUMENTS

| DE | 26 17 007 | 10/1977 |
| JP | 11248696 | 9/1999 |
| RU | 1784898 | 4/1990 |

*Primary Examiner*—Bot LeDynh
(74) *Attorney, Agent, or Firm*—Victor H. Segura; Brigitte L. Echols

(57) ABSTRACT

A well (10) for producing water is characterized in that it includes a network of widely spaced electrodes (8) electrically coupled with measurement means (3) or with electric current generation means (1). By utilizing a measurement result, the progression of a salt water front heading for the well (10) may be detected.

11 Claims, 4 Drawing Sheets

SYSTEM FOR MONITORING SALINITY IN A WATER WELL

The present invention relates to systems for monitoring the salinity of ground water in and around water wells, such as those located near an ocean coast. The invention also relates to the operation of water wells while monitoring salinity.

It is known that wells for drawing ground water located near an ocean coast may become contaminated by salt water and unfit for consumption if the pressure in the well becomes lower than the pressure exerted by the neighboring sea water. The arrival of sea water in the well has serious long term consequences on the delivery of drinking water. Such problems are not restricted to well near to the sea, but can be found when the well is located to other highly saline water sources such as brine reservoirs, etc. The terms "sea water" used in this document encompasses such brines and any other such underground fluids that might contaminate a well so as to make the water produced undrinkable.

Different methods exist for preventing the intrusion of sea water into such wells. The flow rate of drawn water may be limited in order to be sure that the pressure in the ground-water table remains larger than the pressure of sea water. Another method includes recharging the ground-water table from the surface. According to another method, gases under pressure or water are injected into the ground by means of special injection wells. High pressure areas which oppose the advance of sea water in the ground-water table are thereby created in the table.

Observation wells can be provided in the vicinity of the production wells for repeatedly measuring the pressure and salinity of the ground-water table. Since the density of salt water is higher than that of fresh water, the intrusion of salt water often occurs at the lower portion of the water table. Consequently, the salinity of water table is often measured at three levels of the table, a top level, a bottom level and a central level located between the top and bottom levels. Measurement of the salinity at these different levels gives an idea of the efficiency of pumping restrictions or injections made from injection wells in order to prevent sea water intrusion into the water tables.

Samplers that are periodically immersed into the water of a production well or an observation well are used in order to measure the salinity of water. Water picked up in the sampler is brought back to the surface where it is analyzed. Salinity measurement cells may also be used. These cells provide direct in situ measurement of the salinity of the ground water at the location of the cell. In a known way per se, such a cell includes an electrically insulating container in communication with the outside via one or more apertures. The inside of the container includes a set of four electrodes. These four electrodes may be distributed inside the cell either horizontally or vertically. For example, if they are distributed vertically, the arrangement is typically that of a lowermost electrode, an uppermost electrode and two intermediate electrodes located between the lowermost and uppermost electrodes. These electrodes are each connected via an insulated electrical cable to surface equipment, notably current generators, measurement units and computing means for utilizing the collected data. A current is transmitted via wires of the electrical cable between the uppermost and lowermost electrodes (when the electrodes are distributed vertically) which generates a voltage between the intermediate electrodes which depends notably on the conductivity or the resistivity of the water, which itself depends on the salinity of the water. By knowing the injected current, the measured voltage between the intermediate electrodes and other measured or known parameters, in particular the temperature of the water at the measurement location, the salinity of the water present in the well is determined at the level where the cell is located.

In one method for measuring the salinity of the water using salinity measurement cells, the cells are periodically immersed in a production or observation well and the salinity measurement is carried out. The main drawback of this method is that the salinity between two measurement times is not known. Another more recent method consists of providing cells which may be immersed permanently in the wells. These cells may include annular electrodes formed by conducting components positioned around an insulated measurement cable. The annular electrodes are positioned at very small distances from one another, the inter-electrode distances being less than about 5 cm. The annular electrodes are electrically connected to conducting wires of the cable. The measurement may thus be repeated as frequently as desired.

Such a method has no predictive power because the result of the measurement is only influenced by the salinity of the water actually present in the production or observation well. When the presence of salt water is detected, it is already too late, and corrective actions which are taken from the measurement results, can only limit the increase in the salinity.

The invention present invention is directed to a system and method for predicting the arrival of a salt water front by utilizing the results of measurements made in a well before salt water is actually present in the production well. The invention also comprises methods of operating a well to minimize the intrusion of salt water.

The well comprises a cylindrical casing (tubing) positioned either substantially vertically, or deviated from vertical, in the ground and provided with slots allowing the water from outside the casing to penetrate into the well. The well may contain devices, located either permanently or temporarily, for measuring local salinity, comprising measurement cells and/or annular electrodes positioned around the cable, connected to conductor wires of a cable.

The casing is made of an electrically insulating or slightly conductive material (the term electrically insulating is used here in both senses). Electrodes connected to the wires of the cable can be located in the casing, having a much larger inter-electrode spacing than is found between electrodes for measuring local salinity. The spacing between consecutive electrodes of a local measurement network will be of a few centimeters, of the order of 5 cm at most, and the spacing between consecutive electrodes of a network with widely spaced electrodes, will be of the order of several meters, for example between 1.5 and 20 meters.

When the measurement electrodes are close to one another, as in the case of a local measurement of salinity, the lines of electrical current between the intermediate electrodes resulting from the current transmitted between the farthest electrodes can be considered to be concentrated in a volume with a shape determined by the shape of these electrodes and by that of the cell which contains them. Thus, for example, if these electrodes have identical annular shapes, (a circular line) and are positioned above one another, within a cell delimited by an insulating wall, the current lines will mainly be concentrated in a volume for which the envelope surface is the cylindrical surface of the insulating wall of the cell between the farthest electrodes. The leak current lines and the current intensity exiting this volume only have a slight influence on the value of the voltage measured between the intermediate electrodes.

When the distance between electrodes is increased, and if these electrodes are not confined within an electrically insulating cell, the current lines are dispersed in a volume which not only includes the cylindrical volume between the intermediate electrodes, but also a volume which more widely extends around an axis joining the centers of annular electrodes. In particular, many current lines pass through the water via the slots which put the well in communication with the water outside the well. The intensity of the current passing outside the well depends on the distance between the farthest electrodes. In particular, for example, in the case of an increase in salinity in the vicinity of the well, the volumes containing water with more salt have lower resistivities than the volumes containing water with less salt. These volumes of lower resistivity of the water then become preferential sites for concentration of current lines. This displacement of the current lines is expressed by a change in the value of the voltage measured between the intermediate electrodes. Thus, it is possible to see effects beyond the well and detect the approach of a salt water front. If a network is available having more than four electrodes vertically positioned above one another in the well, and widely spaced apart from one another, in the sense indicated earlier, a pair of electrodes of the network may be used as a pair of current-generating electrodes. It is possible to measure the voltage induced by the currents generated by the pair of current-generating electrodes, in each of the intermediate pairs of electrodes. In this way, a set of results from measurements is available for locating a possible salt concentration. Since it is possible to detect the approach of a slat water front in this way, it is then possible, within the scope of the invention, to modify the manner of operation of the well, for example by changing pumping rates or by other actions to maintain or increase reservoir pressure, to stop or slow the advance of the salt water front.

It is noted that considering the rotational symmetry around the well, the location also has rotational symmetry. This means that the actual azimuthal location of the salt concentration is not identified. Predictive models made from multiple measurements under further known salinity conditions do not allow the actual azimuthal location of the salt concentration to be located inside the area of revolution.

However, if a series of wells each equipped in the same way with a network of electrodes is available, then it becomes possible to plot an envelope surface of the different salt concentration locations. With such data obtained by measurement and by calculation on the results of measurement, a shape of a salt front may be determined and corrective operations may therefore be adapted as for example, injection and/or change in the pumping flow rate in the various production wells.

The four electrodes used for a measurement with a wide spacing are not required to be all located deep in the well. One of the current injection electrodes, and/or one of the voltage measurement electrodes may be located at the ground surface.

Thus, the invention relates to a salinity monitoring system for a well including a casing inside which the system is housed, the system including an electrical cable formed by a plurality of conducting wires coated in an insulating material, one end of each wire being connected to an electrode, and the other end of each wire being electrically coupled with measurement devices or with electrical current generating devices, the system being characterized in that the tubing includes apertures distributed along a major portion of its length and is made out of an electrically insulating or weakly conductive material, and in that the spacing between consecutive electrodes to which are connected said conducting wires is sufficiently large for a significant portion of an electric field generated between the electrodes to extend beyond the casing, the spacing typically being larger than one meter.

The electrodes are called widely spaced electrodes.

The wells in which systems according to the invention may be installed can be production wells or observation wells. The apertures in the casing are generally slots, for example longitudinal slots. These apertures place the inside of the well in communication with the outside.

In a first particular embodiment, ends of wires are connected via controllable switches either to a current generator or to measurement device. In this way, the electrodes may be used, either as current-generating electrodes or as voltage measurement electrodes.

Electrode can be located on the external surface of a preferably cylindrical housing. The housing can be mounted on the electrical cable, for example by means of one or more rings clamped on the cable and bearing rigid spokes mechanically secured to the housing.

The cylindrical housing may also houses device(s) for measuring local salinity.

The device for measuring local salinity may comprise current-generating devices and devices that measure voltage between the electrodes, and also include one or more cells for measuring salinity. Each of these cells can include a cell insulating wall with apertures allowing water to flow through the cell insulating wall. Cell electrodes are positioned inside said cell insulating wall, for example as an annular conductor pressed against the wall.

The electrodes for measuring local salinity may also be formed as conductors secured on the outside of the insulating sheath of the cable.

Embodiments of the invention will now be described with reference to the accompanying drawings, in which.

Figure 1:
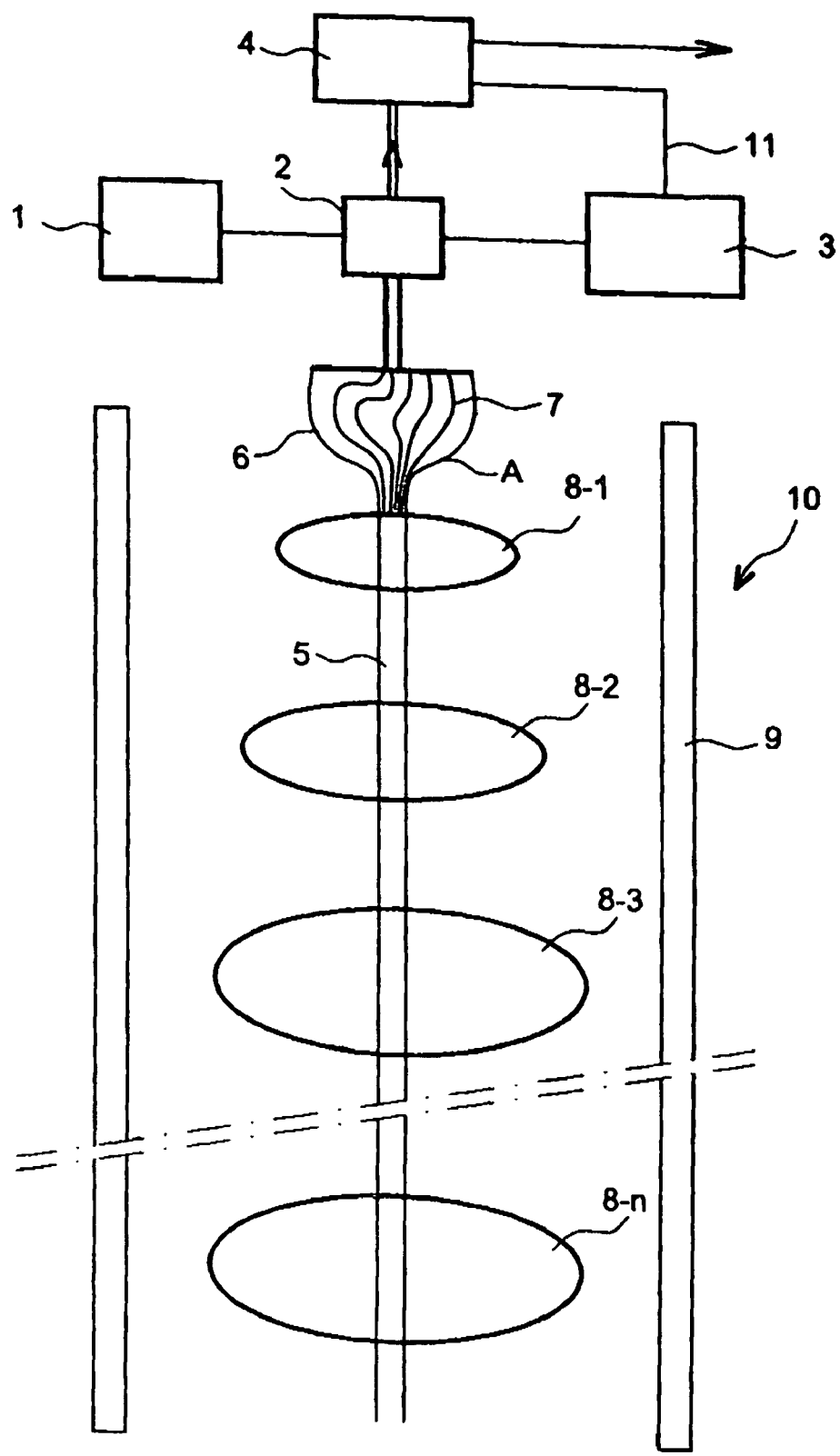
FIG. 1 is a schematic illustration of one embodiment of the invention.

FIG. 1 shows a system for measuring water salinity including an alternate current generator 1, preferably of low frequency in order to limit parasitic inductive and capacitive effects, and a measurement device 3, for measuring electrical voltages. The generator 1 and measurement device 3 are in communication via a switch box 2 with a control and computing system 4, and with an electrical cable 5. The cable 5 is shown in enlarged section A and comprises a sheath 6 and insulated electrical wires 7. Each of the insulated wires 7 is in electrical contact with an electrode 8. There are n electrodes 8 (8-1 to 8-n). The electrodes 8 are regularly spaced apart from one another, although irregular spacing is also possible. The cable 5 is substantially vertical and is located inside a well 10 delimited by a casing 9.

Operation is as follows. The control and computing system 4 include software which provides a power supply for a pair of electrodes selected sequentially from the pairs which may be formed with the n bottom electrodes 8, plus optionally an electrode at the surface (not shown). The selected pair is powered by the generator 1 via the switch box 2 under the control of the control and computing system 4. For each powered pair of electrodes 8, the control and computing system 4 sequentially switches the different pairs of measurement electrodes which may be formed with the unpowered electrodes onto the measurement device 3. One of the measurement electrodes may be located at the surface, but it should be distinct from the surface electrode used for transmitting current, when such an electrode exists. An output 11 of the measurement device 3 is coupled with the control and computing system 4. The results of the different measurements are stored in a memory of the control and computing system 4. When all the measurements are available, the control and computing system 4 establishes an indication of salinity in the vicinity of the well 10.

Figures 2, 6:
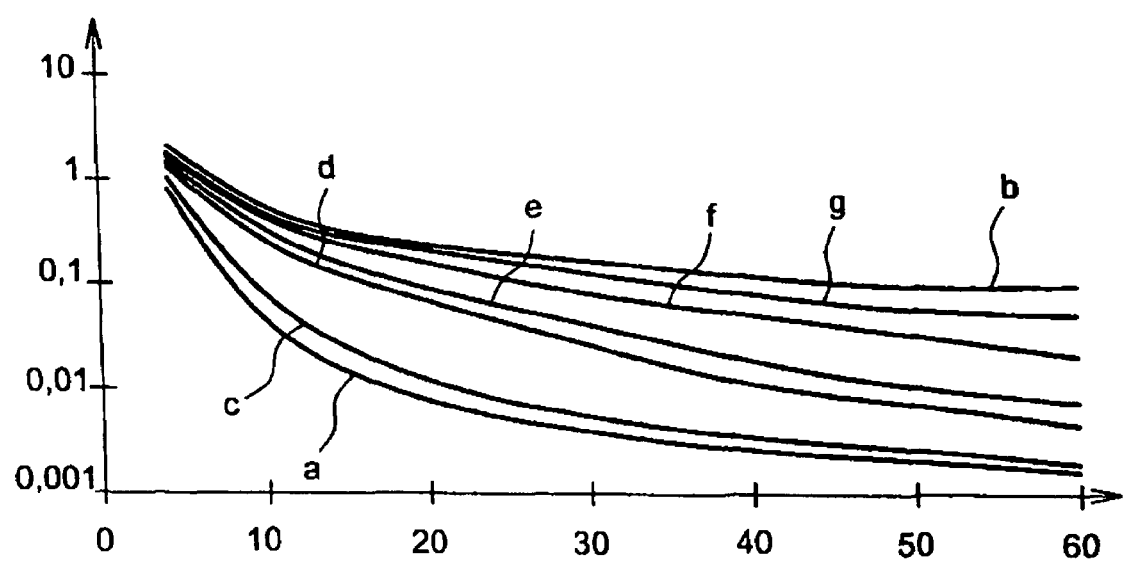
FIG. 2 is a schematic illustration for illustrating a water resistivity calculation.
FIG. 6 is a set of curves, each illustrating the change in a measured ratio versus electrode spacing plotted for a specific distance from the well to a salt front.

The principle on which measurements are based in the case of cells is described here in connection with FIG. 2. This figure illustrates four annular electrodes each delimiting the section S provided by the current, two farthest electrodes A and B and two intermediate electrodes M and N. For example, according to a so-called Wenner configuration, we have: AM=MN=NB=1

A current I is transmitted between the farthest electrodes A and B, and the potential difference $V_M-V_N$ is measured between the intermediate electrodes M and N. When the distance between electrodes is small, as a first approximation, it may be considered that the current density between the intermediate electrodes M and N is uniform and the simple rule which gives the resistance of a conductor of length L of section S and of resistivity $R_W$ may be applied: $(V_M-V_N)/I=R_W L/S$ From the measurement of the current I and of the potential difference $V_M-V_N$ and the dimensions L and S of the cylinder delimited by the M and N electrodes, a value of the resistivity of water $R_W$ is attained, for which the changes are representative of the water's salinity.

When, as in the case of the invention, the distances between electrodes M and N are relatively large, it can no longer be assumed that the current density between the intermediate electrodes M and N is uniform. On the contrary, the heterogeneity of the current densities in the different portions of the volume crossed by the current between the electrodes is used. For example, if it is assumed that the resistivity of a salt water is 100 hundred times lower than the resistivity of fresh water, the arrival of a salt front, for example a vertical front, is expressed by a drop in the apparent measured resistivity. This drop is all the larger as the front is closer. FIG. 6 illustrates a set of curves. Each curve illustrates the change in the ratio between the measured voltage V and the value I of the transmitted current, for a device with a current electrode and a voltage electrode located at the surface. The normalized value, by dividing the V/I ratio by $R_W$ is marked as an ordinate; as an abscissa, the value of the distance between both bottom electrodes is marked in feet. Each of the various curves corresponds to a distance of a salt water front with a resistivity 100 times lower than $R_W$, from the axis of the well 10. The lower curve a represents the normalized value of the W/I ratio when the front is at a distance of 2 feet, about 60 cm, the upper curve b represents the normalized value of the W/I ratio when the front is at a distance of 100 feet, about 30 m. The curves, c, d, e, f, g located between both of these upper and lower curves represent the normalized value of the W/I ratio respectively when the front is at a distance of 3 feet (about 0.9 m), 10 feet (about 3 m), 14 feet (about 4 m), 30 feet (about 9 m), and 75 feet (about 22 m). It is seen that when the distance at which is located the front changes from 30 meters to 0.6 meters, the W/I ratio varies by a factor larger than 10, provided that the spacing between electrodes is larger than 12 feet, about 3.5 m. These curves show that it is possible to calibrate a system for determining the distance of a salt front.

When, as described hereafter, the well 10 is equipped in addition to the widely spaced electrodes, with means for measuring the local salinity at different depths in the well, the calculation of the distance of a salinity front may be improved. The calculation uses a difference or finite element method. Salinity values are repeatedly assigned to localized finite volumes, and it is checked whether these assignments coincide or not with the measured voltage values read out between the various pairs of electrodes. When local measurements of salinity are available, a further constraint is imposed in the sense that the salinities assigned to different finite volumes should be consistent with the salinities measured locally.

Figure 3:
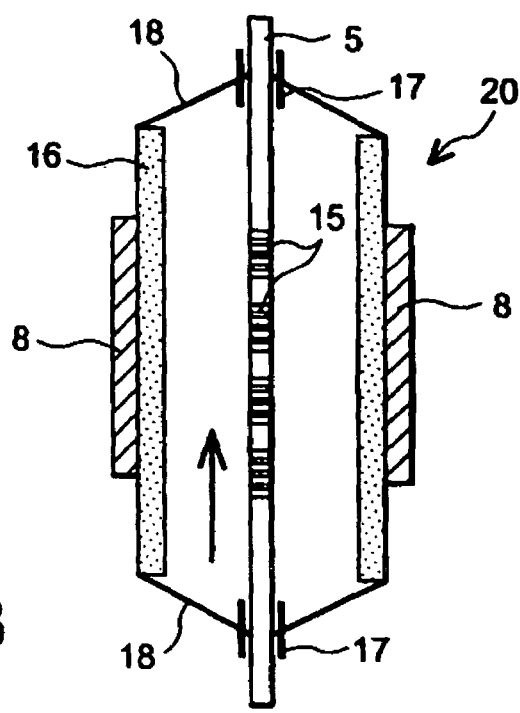
FIG. 3 is a schematic longitudinal section of an embodiment of the invention showing the manner in which electrodes are secured.
Figure 4:
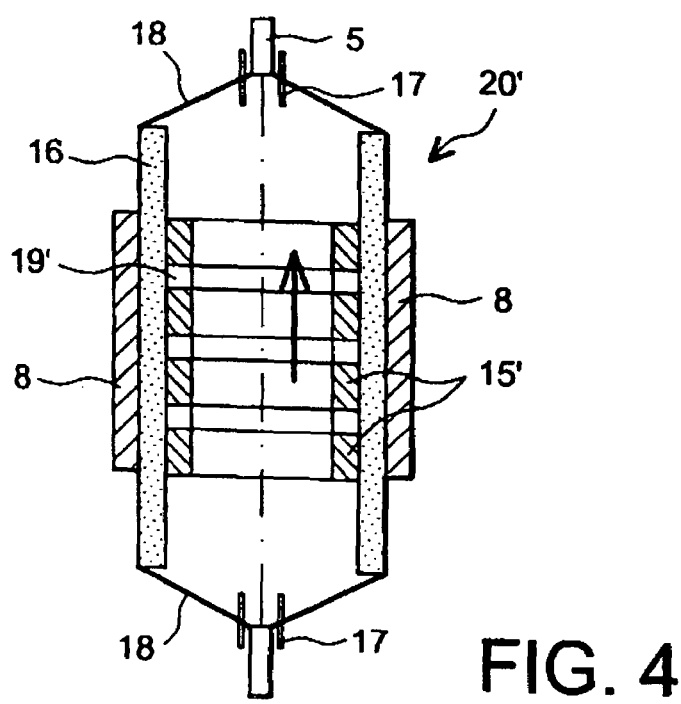
FIG. 4 is a schematic longitudinal section of another embodiment of the invention showing the manner in which electrodes are secured.
Figure 5:
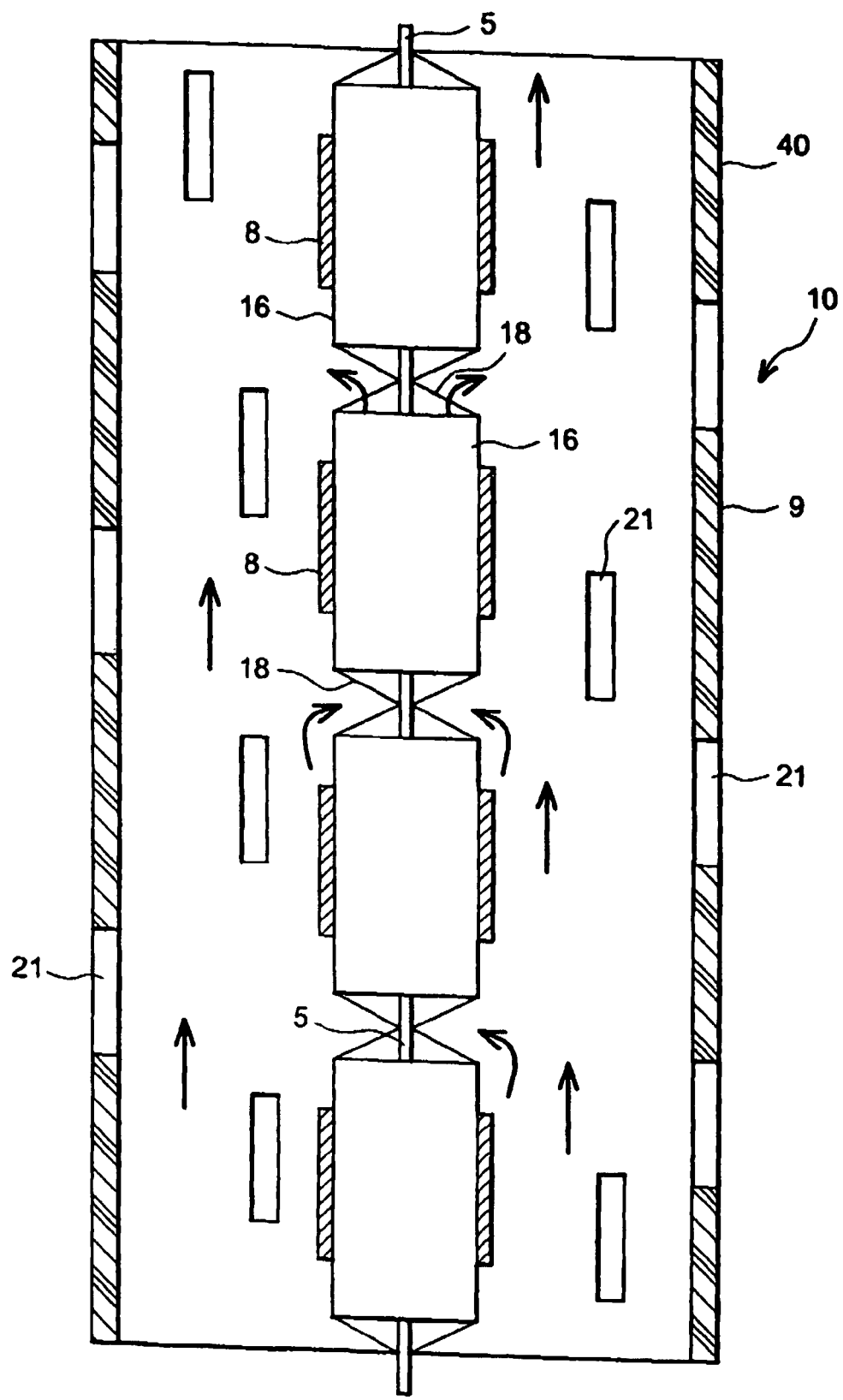
FIG. 5 illustrates a cutaway diagram of a portion of a well showing a set of widely spaced electrodes mounted on means for locally measuring salinity as illustrated in FIG. 3 or 4.

Particular embodiments will now be described in connection with FIGS. 3–5. In FIGS. 3–5, the components with the same function as the components marked on the figures described earlier, bear the same reference number and will not necessarily be described again.

FIG. 3 is a schematic longitudinal section of a first embodiment wherein one takes advantage of the presence of cells 20 for locally measuring salinity in order to secure mechanically the widely spaced electrodes 8. A cell 20 is itself formed by a set of four electrodes 15. The electrodes 15 may appear as a ring or loop, as illustrated in FIG. 3, of a conducting wire, clamped on cable 5. Each of the electrodes 15 of a cell 20 is connected to an end of a conducting wire 7 included in the sheath 6 of cable 5. The spacings between two consecutive electrodes of a cell are approximately equal to each other and lie between 1 and 10 cm. The set of four electrodes 15 is housed within an insulating tube 16 centered on cable 5. The insulating tube 16 is open at both of its ends, so that the water from the well may flow into the tube. The insulating tube 16 is supported and centered on the cable 5 by two rings 17 from which emerge spokes 18. The spokes 18 join the rings 17 at upper and lower ends of the insulating tube 16. The tube 16 bears on its external cylindrical face, an electrode 8 involved in the network of widely spaced electrodes. The electrode 8 appears in the illustrated example, as a conducting coating produced on the external face of the tube 16. The electrode 8 is connected to an end of one of the wires 7 of cable 5. FIG. 4 is also a schematic longitudinal section of a second embodiment wherein one also takes advantage of the presence of a device 20' for locally measuring salinity in order to mechanically secure the widely spaced electrodes 8. In this embodiment, the device comprises a cell 20', as in the example shown earlier. The cell 20' is formed by a set of four electrodes 15' formed as conducting rings secured or coated on the internal face of an insulating tube 16 centered on the cable 5. Each of the electrodes 15' of a cell 20' are connected to one end of a conducting wire 7 included in sheath 6 of cable 5. The spacings between two consecutive electrodes 15' of a cell are equal to each other and lie between 1 and 10 cm. Two consecutive electrodes 15' are separated from each other by insulating rings 19'. As in the example shown in FIG. 3, the set of four electrodes 15' is comprised within the insulating tube 16 centered on cable S. The insulating tube 16 is open at both of its ends, so that the water from the well may flow into the tube. The insulating tube 16 is supported and centered on cable 5 by two rings 17 from which emerge spokes 18 as already explained in connection with FIG. 3. Tube 16 bears on its external cylindrical face, as already explained in connection with FIG. 3, an electrode 8 involved in the network of widely spaced electrodes 8.

FIG. 5 illustrates a well 10, delimited by a cylindrical casing 9 (tubing). A cable 5 bearing a network 40 of widely spaced electrodes 8 is centered in the cylindrical wall 9. The cylindrical casing 9 is bored with slots 21 allowing the ground water to penetrate the well. Each electrode 8 involved in the network, is carried on the external face of a housing 16 with the shape of an insulating tube 16 forming with electrodes 15 or 15' centered within this tube 16, cells 20 or 20' respectively. Unreferenced arrows show the direction of flow of the water in the well and around the insulating tubes 16. In an exemplary embodiment, the network includes 16 regularly spaced electrodes 8. The spacing between two consecutive electrodes is of 4 feet, about 1.2 meters. The spacing between the uppermost electrode and the lowermost electrode is thus of 60 feet, i.e., about 18 meters. Hence, several measurements are possible, according to the selection of the two electrodes used for injecting a current, and of the two electrodes used for measuring the resulting voltage. One of the current electrodes and/or one of the voltage electrodes may be located at the surface. It is noted that electrodes may alternately be electrodes for injecting current or measurement electrodes.

In an another embodiment, the number of widely spaced electrodes 8 is four. Of course, this number may be larger. The number of electrodes 8 should be at least equal to two. In this case, in the well 10, one electrode is used for injecting a current, and one electrode is used for measuring a voltage. A potential reference electrode and an electrode for return of the current are used, located outside and away from the well, for example, at the ground surface.

If several wells are available, either for drawing water or for observation, one or more of them may be equipped with a set of widely spaced electrodes 8, according to one of the embodiments of the invention.

The invention claimed is:

1. A salinity monitoring device for a well including a casing, the device being housed in the casing and comprising an electrical cable having a sheath containing a plurality of conducting wires therein, one end of each wire being connected to an electrode, and the other end of each wire being electrically coupled either to a measurement device or to an electrical current generator, wherein the housing is formed from an electrically insulating material and includes apertures distributed on the major portion of its length, and wherein the spacing between consecutive electrodes is sufficiently large that electrical effect measured thereby are influenced by water surrounding the well beyond the casing in order to predict the arrival of a salt water front.

2. The device of claim 1, wherein the spacing of the electrodes is greater than one meter.

3. The device of claim 1, wherein one end of each wire is connected via a switching system either to the current generator or to the measurement device.

4. The device of claim 2, wherein one end of each wire is connected via a switching system either to the current generator or to the measurement device.

5. The device of claim 1, wherein the electrodes are secured on the outside of the cable.

6. The device of claim 5, wherein the outside of the cable has a device for measuring the local salinity of water in the well located thereon.

7. The device of claim 6, wherein the device for measuring local salinity comprises electrodes located inside a housing secured to the cable.

8. The device of claim 7, wherein the electrodes for measuring local salinity are secured on the sheath of the cable.

9. The device of claim 7, wherein the electrodes for measuring local salinity are secured to the housing.

10. The device of claim 5, wherein the device for measuring local salinity is secured to the cable by means of rings clamped on the cable, spokes being provided to secure the housing to the ring.

11. A salinity monitoring method for a well including a casing comprising the steps of:

housing a salinity monitoring device into the casing, the device comprising an electrical cable having a sheath containing a plurality of conducting wires, one end of each wire being connected to en electrode, and the other end of each wire being electrically coupled either to a measurement device or to an electrical current generator, the device further comprising two farthest electrodes and two intermediate electrodes, the housing being formed from an electrically insulating material and including apertures distributed on the major portion of its length, transmitting a current between the farthest electrodes, measuring the potential between the intermediate electrodes, determining an apparent measured resistivity based on the current the potential and dimensions of the device, wherein the spacing between consecutive electrodes is sufficiently large so that a variation in the apparent measured resistivity is influenced by water surrounding the well beyond the casing, and wherein the method further comprises predicting the arrival of a salt water front based on a drop in the apparent measured resistivity.

* * * * *